(12) United States Patent
Champagne et al.

(10) Patent No.: US 11,191,645 B2
(45) Date of Patent: Dec. 7, 2021

(54) SMALL BONE TAPERED COMPRESSION SCREW

(71) Applicant: ExsoMed Corporation, Phoenix, AZ (US)

(72) Inventors: Lloyd P. Champagne, Phoenix, AZ (US); Jozef Zoldos, Paradise Valley, AZ (US)

(73) Assignee: ExsoMed Corporation, Aliso Viejo, CA (US)

( * ) Notice: Subject to any disclaimer, the term of this patent is extended or adjusted under 35 U.S.C. 154(b) by 0 days.

(21) Appl. No.: 16/122,325

(22) Filed: Sep. 5, 2018

(65) Prior Publication Data

US 2019/0070009 A1 Mar. 7, 2019

Related U.S. Application Data

(60) Provisional application No. 62/554,133, filed on Sep. 5, 2017.

(51) Int. Cl.
*A61F 2/30* (2006.01)
*A61F 2/42* (2006.01)
*A61B 17/72* (2006.01)
*A61B 17/86* (2006.01)

(52) U.S. Cl.
CPC ...... *A61F 2/30771* (2013.01); *A61B 17/7291* (2013.01); *A61B 17/863* (2013.01); *A61F 2/4225* (2013.01); *A61F 2/4241* (2013.01); *A61F 2002/30622* (2013.01); *A61F 2002/30858* (2013.01); *A61F 2002/4228* (2013.01); *A61F 2002/4243* (2013.01)

(58) Field of Classification Search
CPC ............... A61F 2/42; A61F 2002/4228; A61F 2002/4243; A61F 2002/4251; A61F 2/4241; A61F 2002/4233; A61F 2002/4238; A61B 17/8645; A61B 17/8605; A61B 17/863; A61B 17/8004; A61B 17/8014; A61B 2017/8655; A61B 17/84; A61B 17/86
See application file for complete search history.

(56) References Cited

U.S. PATENT DOCUMENTS

| | | | |
|---|---|---|---|
| 1,741,279 A | 12/1929 | Bowman |
| 2,037,586 A | 4/1936 | Olson |
| 2,210,455 A | 8/1940 | Hosking |
| 2,217,951 A | 10/1940 | Hosking |
| 2,229,892 A | 1/1941 | Hosking |
| 2,242,003 A | 5/1941 | Lorenzo |

(Continued)

FOREIGN PATENT DOCUMENTS

| | | |
|---|---|---|
| CH | 643131 | 5/1984 |
| CH | 646858 | 12/1984 |

(Continued)

*Primary Examiner* — Alvin J Stewart
(74) *Attorney, Agent, or Firm* — Knobbe, Martens, Olson & Bear, LLP

(57) ABSTRACT

The present invention relates to a device and system for surgical fixation of small bones, small bone fragments, and osteotomies and more particularly to compression screw having an elongated and spiked tapered threaded leading portion which is joined to a section that is free from threads and a threaded trailing portion and more sharply tapered head which has threads that continue from the threads of the leading portion.

14 Claims, 3 Drawing Sheets

(56) References Cited

U.S. PATENT DOCUMENTS

| | | | |
|---|---|---|---|
| 3,275,055 A | 9/1966 | Gutshall | |
| 3,397,699 A | 8/1968 | Kohl | |
| 3,717,146 A | 2/1973 | Halloran | |
| 4,016,874 A | 4/1977 | Maffei | |
| 4,175,555 A | 11/1979 | Herbert | |
| 4,380,414 A | 4/1983 | Capuano | |
| 4,463,753 A * | 8/1984 | Gustilo | A61B 17/863 411/386 |
| 4,471,777 A | 9/1984 | McCorkle | |
| 4,584,722 A | 4/1986 | Levy et al. | |
| 4,608,965 A | 9/1986 | Anspach | |
| 4,764,066 A | 8/1988 | Terrell | |
| 4,781,191 A | 11/1988 | Thompson | |
| 4,812,095 A | 3/1989 | Piacenti | |
| 4,901,717 A | 2/1990 | Moore et al. | |
| 4,909,789 A | 3/1990 | Taguchi et al. | |
| 5,061,283 A | 10/1991 | Silvestrini | |
| 5,074,790 A | 12/1991 | Bauer | |
| 5,234,299 A | 8/1993 | Giannuzzi | |
| 5,312,255 A | 5/1994 | Bauer | |
| 5,345,927 A | 9/1994 | Bonutti | |
| 5,443,466 A | 8/1995 | Shah | |
| 5,645,545 A | 7/1997 | Bryant | |
| 5,667,510 A | 9/1997 | Combs | |
| 5,690,633 A | 11/1997 | Taylor et al. | |
| 5,853,413 A | 12/1998 | Carter et al. | |
| 6,001,101 A * | 12/1999 | Augagneur | A61B 17/863 606/316 |
| 6,019,762 A * | 2/2000 | Cole | A61B 17/8047 606/104 |
| 6,187,007 B1 | 2/2001 | Frigg | |
| 6,221,006 B1 | 4/2001 | Dubrul et al. | |
| 6,231,319 B1 | 5/2001 | Iida et al. | |
| 6,231,413 B1 | 5/2001 | Tsukamoto | |
| 6,306,140 B1 * | 10/2001 | Siddiqui | A61B 17/863 606/315 |
| 6,319,254 B1 * | 11/2001 | Giet | A61B 17/863 606/104 |
| 66,475,242 | 11/2002 | Bramlet | |
| 6,517,541 B1 | 2/2003 | Sesic | |
| 6,592,623 B1 | 7/2003 | Bowlin et al. | |
| 6,607,530 B1 | 8/2003 | Carl et al. | |
| 6,808,526 B1 | 10/2004 | Magerl et al. | |
| 7,041,106 B1 | 5/2006 | Carver et al. | |
| 7,334,976 B2 | 2/2008 | Dicke | |
| 7,465,135 B2 | 12/2008 | Fritsch | |
| 7,507,242 B2 | 3/2009 | Triplett et al. | |
| 7,708,738 B2 * | 5/2010 | Fourcault | A61B 17/863 606/67 |
| 7,766,942 B2 | 8/2010 | Patterson | |
| 7,988,724 B2 | 8/2011 | Salahieh et al. | |
| 8,011,866 B2 | 9/2011 | Harris | |
| 8,105,367 B2 * | 1/2012 | Austin | A61B 17/8057 606/280 |
| 8,118,849 B2 * | 2/2012 | Wahl | A61B 17/8605 606/305 |
| 8,157,803 B1 | 4/2012 | Zirkle, Jr. | |
| 8,398,687 B2 | 3/2013 | Vasta et al. | |
| 8,398,690 B2 * | 3/2013 | Bottlang | A61B 17/8057 606/308 |
| 8,414,648 B2 | 4/2013 | Reiley | |
| 8,419,776 B2 | 4/2013 | Prandi et al. | |
| 8,518,042 B2 | 8/2013 | Winsow et al. | |
| 8,568,462 B2 | 10/2013 | Sixto et al. | |
| 8,597,337 B2 | 12/2013 | Champagne | |
| 8,608,783 B2 | 12/2013 | Graham et al. | |
| 8,734,462 B2 * | 5/2014 | Reiley | A61B 17/1659 606/105 |
| 8,814,918 B2 | 8/2014 | Orbay et al. | |
| 8,852,253 B2 | 10/2014 | Mafi | |
| 8,864,804 B2 * | 10/2014 | Champagne | A61B 17/863 606/309 |
| 8,888,429 B2 | 11/2014 | Pamer | |
| 8,906,075 B2 | 12/2014 | Conley et al. | |
| 8,945,193 B2 * | 2/2015 | Kirschman | A61B 17/7064 606/304 |
| 9,011,505 B2 * | 4/2015 | Prandi | A61B 17/8635 606/315 |
| 9,017,404 B2 | 4/2015 | Champagne et al. | |
| 9,046,120 B2 | 6/2015 | Phua | |
| 9,078,716 B2 * | 7/2015 | Pech | A61B 17/7225 |
| 9,175,715 B2 | 11/2015 | Babej | |
| 9,265,600 B2 | 2/2016 | Niese | |
| 9,480,515 B2 | 11/2016 | Champagne | |
| 9,482,260 B1 | 11/2016 | Krause | |
| 9,539,084 B2 | 1/2017 | Champagne | |
| 9,642,656 B2 * | 5/2017 | Kotuljac | A61B 17/7291 |
| 9,687,284 B2 * | 6/2017 | Pancheco | A61B 17/866 |
| 9,724,140 B2 | 8/2017 | McCormick | |
| 9,848,927 B2 * | 12/2017 | Giorno | A61C 8/0022 |
| 9,861,413 B2 | 1/2018 | Palmer et al. | |
| 9,980,759 B2 * | 5/2018 | Lavi | A61B 17/72 |
| 10,058,368 B2 * | 8/2018 | Orbay | A61B 17/863 |
| 10,080,597 B2 | 9/2018 | Shemwell et al. | |
| 10,098,680 B2 | 10/2018 | Champagne | |
| 10,136,929 B2 * | 11/2018 | Fallin | A61B 17/7291 |
| 10,245,091 B2 * | 4/2019 | Champagne | A61B 17/7291 |
| 10,499,960 B2 | 12/2019 | Sinnott et al. | |
| 10,610,276 B2 * | 4/2020 | Lutz | A61B 17/8685 |
| 2001/0049529 A1 | 12/2001 | Cachia et al. | |
| 2002/0045897 A1 | 4/2002 | Dixon et al. | |
| 2002/0055747 A1 | 5/2002 | Cano et al. | |
| 2002/0055749 A1 | 5/2002 | Esnouf et al. | |
| 2002/0143337 A1 | 10/2002 | Orbay et al. | |
| 2002/0198527 A1 | 12/2002 | Muckter | |
| 2003/0014077 A1 | 1/2003 | Leung | |
| 2003/0083661 A1 | 5/2003 | Orbay et al. | |
| 2003/0130735 A1 | 7/2003 | Rogalski | |
| 2004/0193217 A1 | 9/2004 | Lubbers | |
| 2004/0210227 A1 * | 10/2004 | Trail | A61B 17/863 606/916 |
| 2004/0260288 A1 | 12/2004 | Means | |
| 2005/0075642 A1 | 4/2005 | Felt | |
| 2005/0085824 A1 | 4/2005 | Castaneda | |
| 2005/0107791 A1 | 5/2005 | Manderson | |
| 2005/0143735 A1 | 6/2005 | Kyle | |
| 2006/0129153 A1 | 6/2006 | Klaue et al. | |
| 2006/0149249 A1 | 7/2006 | Mathoulin et al. | |
| 2006/0165506 A1 | 7/2006 | Panasik | |
| 2006/0195099 A1 | 8/2006 | Bottlang | |
| 2006/0271061 A1 | 11/2006 | Beyar | |
| 2006/0276790 A1 | 12/2006 | Dawson | |
| 2007/0027547 A1 | 2/2007 | Rydell et al. | |
| 2007/0135816 A1 | 6/2007 | Kropf et al. | |
| 2007/0233123 A1 * | 10/2007 | Ahmad | A61B 17/863 606/307 |
| 2007/0282342 A1 | 12/2007 | Niederberger et al. | |
| 2007/0299449 A1 | 12/2007 | Allinniemi et al. | |
| 2008/0183220 A1 | 7/2008 | Glazer | |
| 2008/0219801 A1 | 9/2008 | Toenjes | |
| 2008/0249547 A1 | 10/2008 | Dunn | |
| 2008/0249574 A1 | 10/2008 | McCombs et al. | |
| 2008/0287958 A1 | 11/2008 | Logan et al. | |
| 2008/0300639 A1 * | 12/2008 | Martin | A61B 17/863 606/315 |
| 2009/0062868 A1 | 3/2009 | Casutt | |
| 2009/0149890 A1 | 6/2009 | Martin | |
| 2009/0240291 A1 * | 9/2009 | Gorek | A61B 17/7032 606/316 |
| 2009/0299369 A1 | 12/2009 | Orbay et al. | |
| 2009/0306718 A1 | 12/2009 | Tipirneni et al. | |
| 2010/0106254 A1 | 4/2010 | Delsignore | |
| 2010/0121136 A1 | 5/2010 | Champagne | |
| 2010/0130978 A1 | 5/2010 | Orbay et al. | |
| 2010/0174323 A1 * | 7/2010 | Fourcault | A61B 17/863 606/304 |
| 2010/0211115 A1 | 8/2010 | Tyber et al. | |
| 2010/0312286 A1 | 12/2010 | Dell'Oca | |
| 2010/0312292 A1 | 12/2010 | Tipirneni et al. | |
| 2010/0324556 A1 | 12/2010 | Tyber et al. | |
| 2011/0009865 A1 | 1/2011 | Orfaly | |

(56) References Cited

U.S. PATENT DOCUMENTS

| | | | |
|---|---|---|---|
| 2011/0118795 A1* | 5/2011 | Hashmi | A61B 17/863 606/308 |
| 2011/0130794 A1 | 6/2011 | Vaidya | |
| 2011/0144644 A1 | 6/2011 | Prandi et al. | |
| 2011/0144703 A1 | 6/2011 | Krause et al. | |
| 2011/0276095 A1* | 11/2011 | Bar | A61B 17/863 606/279 |
| 2011/0313473 A1* | 12/2011 | Prandi | A61B 17/863 606/315 |
| 2012/0083847 A1* | 4/2012 | Huebner | A61B 17/8057 606/281 |
| 2012/0136398 A1 | 5/2012 | Mobasser | |
| 2012/0191140 A1 | 7/2012 | Bonutti | |
| 2012/0197311 A1* | 8/2012 | Kirschman | A61B 17/7098 606/304 |
| 2012/0221104 A1 | 8/2012 | Altman et al. | |
| 2012/0232599 A1* | 9/2012 | Schoenly | A61F 2/4455 606/315 |
| 2012/0253464 A1 | 10/2012 | Hwang et al. | |
| 2012/0253465 A1 | 10/2012 | Missos | |
| 2013/0012987 A1 | 1/2013 | Klein et al. | |
| 2013/0053961 A1 | 2/2013 | Darwin et al. | |
| 2013/0060333 A1 | 3/2013 | Gonzalez | |
| 2013/0131699 A1 | 5/2013 | Jiango et al. | |
| 2013/0138123 A1 | 5/2013 | Stone et al. | |
| 2013/0165979 A1 | 6/2013 | Greenberg et al. | |
| 2013/0190872 A1 | 7/2013 | Makower et al. | |
| 2013/0197592 A1 | 8/2013 | Mafi | |
| 2013/0245626 A1* | 9/2013 | Lavi | A61B 17/72 606/62 |
| 2013/0245700 A1 | 9/2013 | Choinski | |
| 2013/0245762 A1 | 9/2013 | Van Kampen et al. | |
| 2013/0261662 A1 | 10/2013 | Mayer et al. | |
| 2013/0274789 A1 | 10/2013 | Brooks et al. | |
| 2013/0274879 A1 | 10/2013 | Champagne et al. | |
| 2013/0282058 A1 | 10/2013 | ElAttrache et al. | |
| 2013/0325011 A1 | 12/2013 | Cleveland et al. | |
| 2014/0025124 A1 | 1/2014 | Champagne et al. | |
| 2014/0067063 A1 | 3/2014 | Bonutti | |
| 2014/0155943 A1* | 6/2014 | Andersen | A61B 17/863 606/312 |
| 2014/0257349 A1 | 9/2014 | Sudekum | |
| 2014/0276846 A1 | 9/2014 | Mauldin | |
| 2014/0309747 A1* | 10/2014 | Taylor | A61B 17/846 623/21.11 |
| 2014/0336712 A1 | 11/2014 | Strnad et al. | |
| 2015/0066060 A1 | 3/2015 | Bojarski | |
| 2015/0094722 A1 | 4/2015 | Champagne et al. | |
| 2015/0094724 A1 | 4/2015 | Champagne et al. | |
| 2015/0094777 A1 | 4/2015 | Champagne et al. | |
| 2015/0173737 A1 | 6/2015 | Champagne et al. | |
| 2015/0182325 A1 | 7/2015 | Champagne et al. | |
| 2015/0201978 A1 | 7/2015 | Piccin | |
| 2015/0201984 A1* | 7/2015 | Orbay | A61B 17/863 606/304 |
| 2015/0374503 A1* | 12/2015 | Lovick | A61B 17/7291 623/23.5 |
| 2016/0030097 A1 | 2/2016 | Mildner et al. | |
| 2016/0045324 A1 | 2/2016 | Austin et al. | |
| 2016/0213413 A1* | 7/2016 | Hientzsch | A61B 17/863 |
| 2016/0256290 A1 | 9/2016 | Seavey et al. | |
| 2016/0278833 A1* | 9/2016 | Wong | A61B 17/8645 |
| 2016/0287300 A1* | 10/2016 | McCormick | A61B 17/7291 |
| 2016/0296263 A1 | 10/2016 | Champagne et al. | |
| 2016/0296264 A1 | 10/2016 | Champagne et al. | |
| 2016/0310187 A1* | 10/2016 | Leibinger | A61B 17/7032 |
| 2016/0338748 A1 | 11/2016 | Champagne et al. | |
| 2017/0014170 A1* | 1/2017 | Fallin | A61B 17/7291 |
| 2017/0027577 A1 | 2/2017 | Kubiak et al. | |
| 2017/0035553 A1 | 2/2017 | Champagne et al. | |
| 2017/0049167 A1 | 2/2017 | Champagne et al. | |
| 2017/0065424 A1* | 3/2017 | Lauf | A61B 17/7291 |
| 2017/0112555 A1* | 4/2017 | Wallenstein | A61B 17/7082 |
| 2017/0151061 A1 | 6/2017 | Lavi | |
| 2017/0189090 A1 | 7/2017 | Champagne | A61B 17/7291 |
| 2017/0196608 A1* | 7/2017 | Castaneda | A61B 17/863 |
| 2017/0196609 A1* | 7/2017 | Champagne | A61B 17/864 |
| 2017/0196612 A1* | 7/2017 | Castaneda | A61B 17/8645 |
| 2017/0239059 A1 | 8/2017 | Boublil et al. | |
| 2017/0319349 A1 | 11/2017 | Kowalczyk | |
| 2017/0325827 A1 | 11/2017 | Champagne et al. | |
| 2018/0008317 A1* | 1/2018 | Sinha | A61B 17/68 |
| 2018/0021124 A1 | 1/2018 | Champagne et al. | |
| 2018/0049881 A1* | 2/2018 | Austin | A61F 2/30771 |
| 2018/0092677 A1 | 4/2018 | Peterson et al. | |
| 2018/0263669 A1 | 9/2018 | Peterson et al. | |
| 2018/0303529 A1* | 10/2018 | Zastrozna | A61B 17/8605 |
| 2018/0317989 A1 | 11/2018 | Sellers | |
| 2019/0070013 A1* | 3/2019 | Champagne | A61F 2/4241 |
| 2019/0210016 A1 | 7/2019 | Zhong et al. | |
| 2019/0262047 A1* | 8/2019 | Sommers | A61B 17/8625 |
| 2019/0321087 A1* | 10/2019 | Wapner | A61B 17/866 |

FOREIGN PATENT DOCUMENTS

| | | |
|---|---|---|
| DE | 2713386 | 11/1978 |
| DE | 102007003645 | 7/2008 |
| DE | 2020131101135 U1 | 7/2014 |
| EP | 0597223 | 5/1994 |
| EP | 1378205 | 1/2004 |
| EP | 2606843 | 6/2013 |
| GB | 2007099 | 5/1979 |
| GB | 2181356 | 4/1987 |
| WO | 9733537 A1 | 9/1997 |
| WO | 2004093700 A1 | 11/2004 |
| WO | 2005092226 A1 | 10/2005 |
| WO | 2006105935 A1 | 10/2006 |
| WO | WO 2007/081601 | 7/2007 |
| WO | 2007109140 A1 | 9/2007 |
| WO | WO 2008/063156 | 5/2008 |
| WO | WO 2010/151589 | 12/2010 |
| WO | WO 2012/050424 | 4/2012 |
| WO | WO 2014/011933 | 1/2014 |
| WO | WO 2014/089522 | 6/2014 |
| WO | WO 2015/050895 | 9/2015 |
| WO | WO 2015/050896 | 9/2015 |
| WO | WO 2015/050898 | 9/2015 |
| WO | WO 2015/050900 | 9/2015 |
| WO | WO 2015/050902 | 9/2015 |
| WO | WO 2016/186847 | 11/2016 |

* cited by examiner

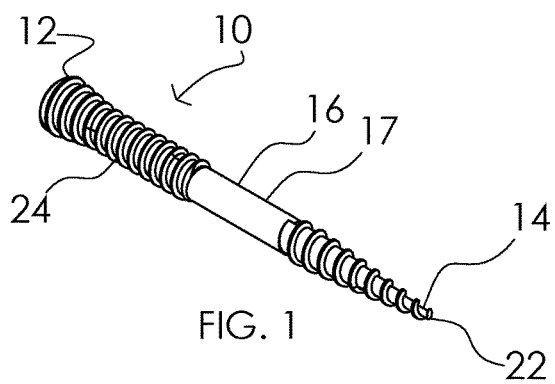
FIG. 1
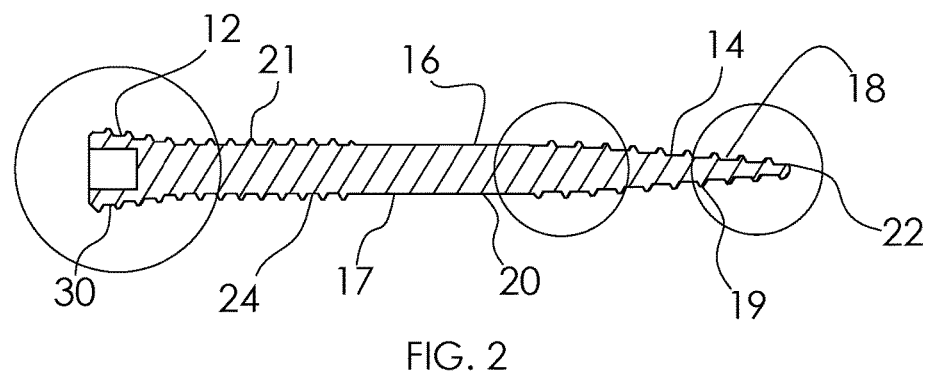
FIG. 2
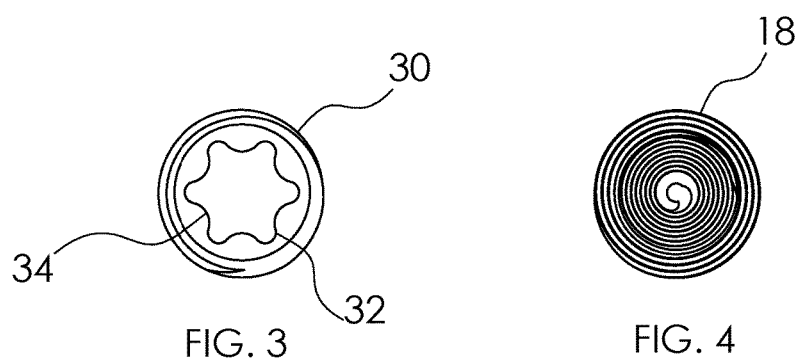
FIG. 3
FIG. 4
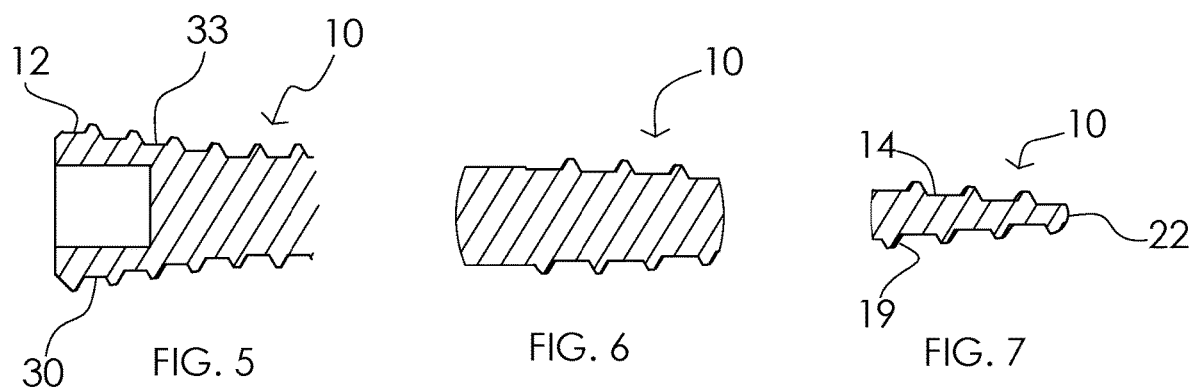
FIG. 5
FIG. 6
FIG. 7

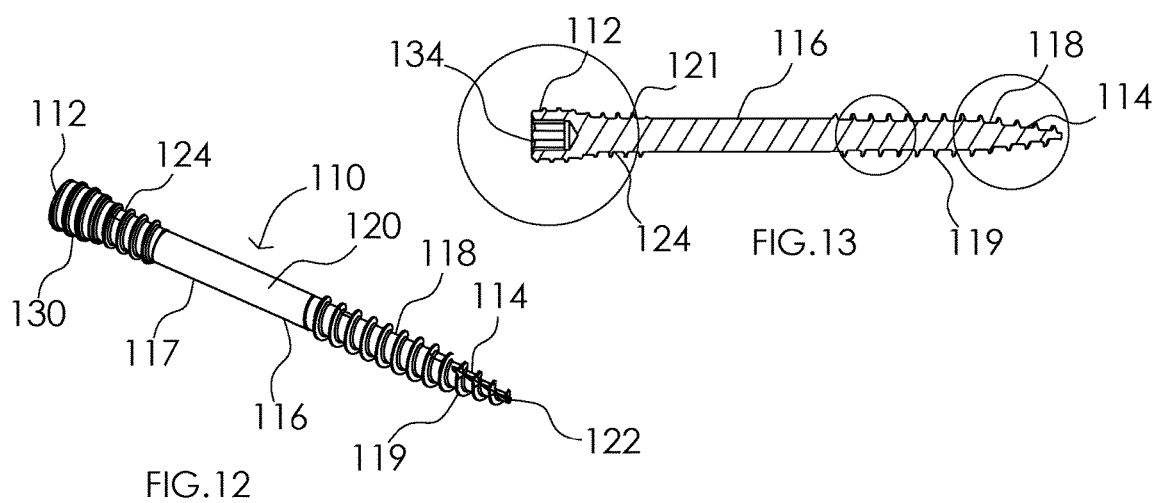
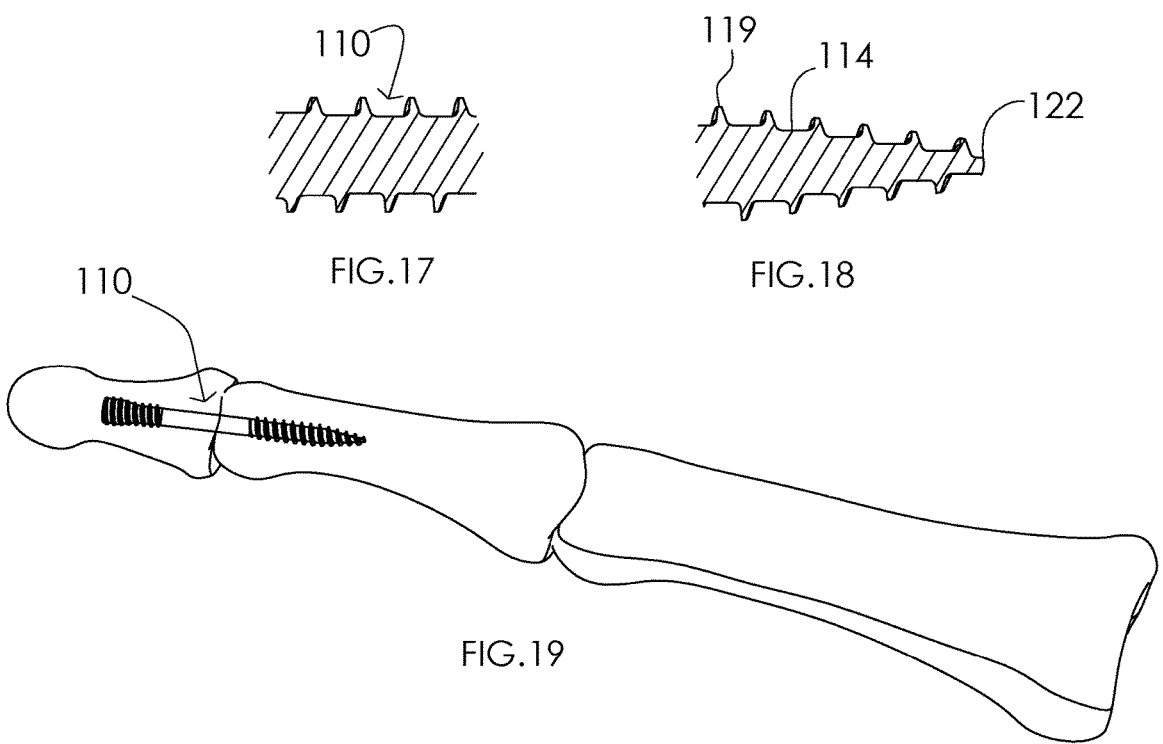

SMALL BONE TAPERED COMPRESSION SCREW

FIELD OF THE INVENTION

The present invention relates to a device and system for surgical fixation of small bones, small bone fragments, and osteotomies and more particularly to compression screw having an elongated and slowly tapered threaded leading portion which is joined to a section that is free from threads and a threaded trailing portion and more sharply tapered head which has threads that continue from the threads of the leading portion.

BACKGROUND OF THE INVENTION

Patients often suffer from late stage arthritis in phalangeal joints of the hands and feet, and this presents a variety of challenges for attending physicians. While current treatment protocols usually provide acceptable results, there is a likelihood of straight distal interphalangeal joint fusion which provides for sub-optimal outcomes. Research has shown that when a patient's distal interphalangeal joint is fused in a functional position, finger dexterity and grip strength improve over that of a patient with a straight fusion. Physicians can achieve angled fusions by using k-wire fixation, however, this immobilization protocol can fail, and lead to several complications and varied results. While the utilization of compression screws can provide reliable, strong repairs, it does not offer the additional benefit of function flexion which is provide by a properly angled and oriented implant fixation device, especially one, which provides the added benefit of compression across the joint during fusion.

Advantageous locations the use of the present invention is in the phalanges of the hand or foot. In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint. The joints are covered on the ends with articular cartilage. The foot has an analogous structure substituting the large toe for the thumb. It should be understood that there may be additional surgical techniques or locations in the body where the device of the present invention may be suitable for use.

SUMMARY OF THE INVENTION

The present invention solves the problems associated with performing a fusion technique or an osteotomy, in particular in the interphalangeal joints. The device of the invention is a compression screw having a shaft with a longitudinal axis along which there is a leading portion including a sharp spiked threaded tip, and an intermediate unthreaded portion, and a trailing threaded portion which joins the intermediate portion and the more sharply expanding or tapered head portion, which may include the same thread pitch, size and shape of the trailing shaft portion having a constant inner diameter and outer diameter. Alternatively, the trailing portion may have a lesser thread pitch compared to the tapered tip. It should be noted while that the trailing portion may be considered to be proximal to the leading portion relative to the screw itself, in use, the leading portion is intended to be implanted more proximally relative to the joint than the trailing portion. Moreover, the head portion is configured to provide for compression across the fusion joint, and to inhibit rotation of the compression device in the interphalangeal position as the leading portion is embedded into the intermediate phalange which is positioned at an angle with respect to the distal phalange. In addition, the present invention by provides for a percutaneous insertion in a surgical technique with an intramedullary implant designed to minimize soft tissue, cartilage and vascular damage upon insertion; and to facilitate early, active mobilization post-operative protocols for accelerated healing and earlier return to work.

The head at the trailing end includes a driving recess, such as a hexalobe, capable of being driven by a suitable driver into the opening.

BRIEF DESCRIPTION OF THE DRAWINGS

FIG. 1 is an isometric view of a device in accordance with the invention;

FIG. 2 is a side cross-sectional view of the device of FIG. 1 taken along the longitudinal central axis;

FIG. 3 is an end view of the head of the device from the trailing end;

FIG. 4 is an end view of the device from the leading end;

FIG. 5 is a detail of FIG. 2 showing the threads and the head;

FIG. 6 is a detail of FIG. 2 showing the top of the threaded leading section;

FIG. 7 is a detail of FIG. 2 showing the steeply tapered spike end of the screw of FIG. 2;

FIG. 12 is an isometric view of a further embodiment of the device in accordance with the invention;

FIG. 13 is a side cross-sectional view of the device of FIG. 12 taken along the longitudinal central axis;

FIG. 14 is an end view of the head of the device of FIG. 12 from the trailing end;

FIG. 15 is an end view of the device of FIG. 12 from the leading end;

FIG. 16 is a detail of FIG. 12 showing the threads and the head;

FIG. 17 is a detail of FIG. 12 showing the far end of the threaded leading section;

FIG. 18 is a detail of FIG. 12 showing the steeply tapered spike end of the screw of FIG. 12; and FIG. 19 is a dorsal view of a skeleton of a hand showing the implant of the invention of FIG. 12 in place in a PIP fusion.

DETAILED DESCRIPTION OF THE INVENTION

Figure 8:
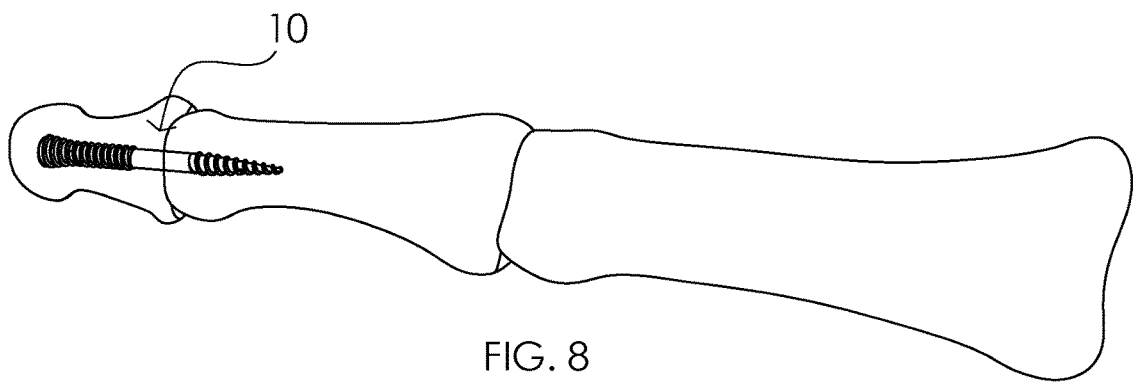
FIG. 8 is a dorsal view of a skeleton of a hand showing the implant of the invention in place in a PIP fusion.

FIG. 1 shows an exemplary embodiment 10 of the tapered compression screw of the present invention. The screw 10 may be formed of any suitable biocompatible material, such as surgical grade stainless steel, titanium, alloys of nickel and chromium, nitinol, PEEK, hydroxyapatite, bio-glass or other bio compatible materials or combinations of these materials. The screw 10 has a first end, or trailing end (i.e. relative to the screw, the proximal end), 12, a second end, or leading end (again relative to the screw, the distal end), 14, a shaft 16 with an outer surface 17, and the shaft 16 including a slowly tapered spiked leading portion (i.e. a long cone) 18 which includes a thread 19 and a terminal end 22. The leading portion 18 is joined to an intermediate portion of the shaft 20 which is free from threads and is joined to a trailing portion 24 of the shaft 16. The trailing portion 24 has threads 21 and joins the leading portion 18 of the shaft to a compression head 30 which also includes threads 23 at the same pitch and shape as the threads 21 of the trailing portion (although in a further embodiment, the thread pitch may be changed to achieve greater compression). The head 30 also forms a cone 33 that is threaded, and which joins the threaded cylindrical portion of the trailing section of the shaft 16. The head 30 has a driving surface 32 in a drive recess 34 formed in the top of first end 12.

The angle of the leading tapered area is from 4° to 12°, and preferably 5-8° which is defined at the intersection of a line at the outer surface of the inner diameter of the leading area and the central axis and the compression head has an angle which is similarly determined and is from 5° to 16°, but preferably is 9-14°, and is at least 2° greater than the taper of the leading end and extends for a distance longitudinally that is 25% to 75% of the distance of the leading taper. Ideally, the leading taper extends for from 25% to 50% of the length of the screw, and the intermediate portion extends of 25% to 50% of the length and the trailing portion of the shaft extends for 15% to 50% of the length of the screw and the head extends for 5% to 15% of the length of the screw, with the screw shaft nominally comprising ⅓ trailing portion, ⅓ intermediate portion and ⅓ leading portion+/−5-10% for each portion.

The spiked end can be driven into the intermediate phalange at an angle to create the position of functional flexion. The aggressive taper on the leading tip allows the screw to be used in facilitating angulation between two bone while still fitting into the bone, which the prior art screws do not accommodate. The driving surface 32 of the head has a hexalobe drive configuration, although any suitable driving configuration may be used. Other driving configurations that may be used include slotted, Pozidriv, Robertson, tri-wing, Torq-Set, SpannerHead, Triple Square and hex head.

The leading and trailing portions of the device includes a thread which is defined between the outer diameter and the inner diameter and can suitably include a right handed single start thread with a pitch of from 3-4, and preferably at 3+/−0.5 with a similar lead value. In the second embodiment the tip pitch is from 0.9 to 1.0 mm and preferably 0.95+/−0.02 mm, and the head pitch is from 0.70 to 0.85 mm, and preferably 0.75 mm The trailing section and following profiles of the threads together form an angle of 25° to 75° and preferably 30°+/−15°, and preferably +/−10°, and with a thread depth of 0.1 mm to 0.4 mm+/−0.02 mm, and optionally a thrust profile or a traditional bone screw buttress thread. There is a pitch differential between the threads of the conical section of the head and the spiked taper of the leading end of the screw, with the leading thread pitch being about 0.75 to 1.25, but in any case, from 1.2 to 1.5 times the pitch of the compression head, which is 0.5 to 1.0.

FIG. 8 illustrates a screw 10 in accordance with the present invention in position across a first PIP joint to secure a fusion.

Figure 9:
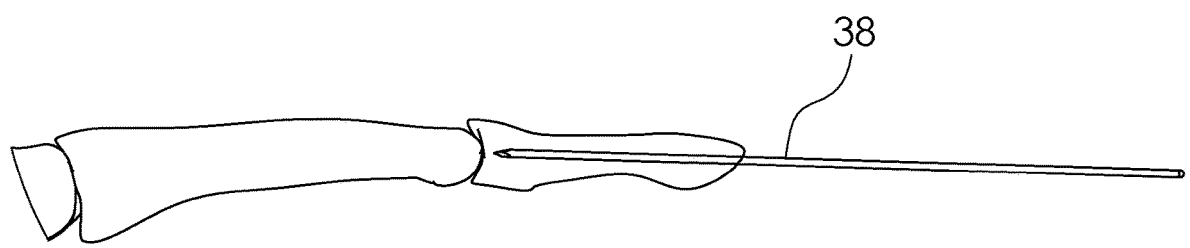
FIG. 9 is an illustration of the step of inserting a guide wire in a retrograde fashion through the distal phalange in accordance with the technique of the invention.
Figure 10:
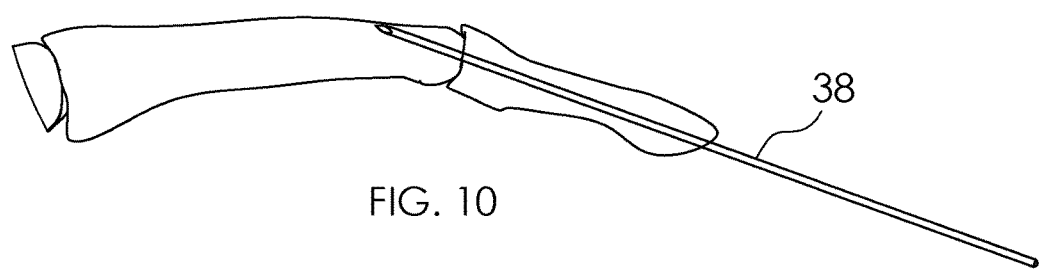
FIG. 10 is an illustration of the step of inserting a guide wire in a retrograde fashion through the intermediate phalange in function flexion accordance with the technique of the invention.

In FIG. 9, in a first step of a surgical technique in accordance with the invention, the joint is scored for fusion and a guide wire 38 is inserted in the intramedullary cannel in retrograde until is abuts the inners cortical surface of the distal phalange, In FIG. 10 the end of the finger is bent and the guide wire is inserted further into the phalanges to secure the distal phalange in a position of functional flexion relative to the intermediate phalange. A cannulated drill can be used to drill a hole across the fusion site over the guide wire.

Figure 11:
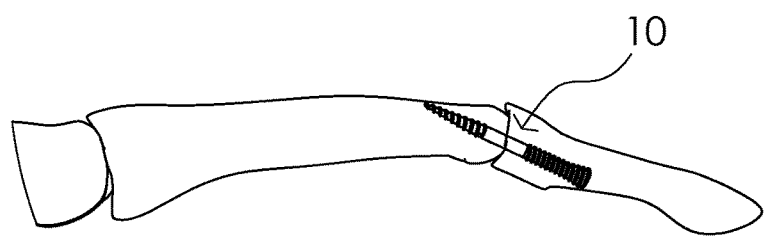
FIG. 11 is an illustration of the step of inserting and confirming the placement of the implant across the fusion site in accordance with the surgical technique of the invention.

In FIG. 11, the device 10 is driven into the opening in the phalanges by means of the drive recess. The outer diameter of the threads 28, is slightly larger than the inner diameter of the opening in the bone. This provides bone material for threads 28 to thread into and provides a tight fit for device 10.

FIG. 12-19 show a second embodiment 110 of the tapered compression screw of the present invention. This screw 110 has a first end, or trailing end (i.e. relative to the screw, the trailing end), 112, a second end, or leading end (again relative to the screw, the leading end), 114, a shaft 116 with an outer surface 117, and the shaft 116 including a slowly tapered spiked leading portion (i.e. a long cone) 118 which includes a thread 119 and a terminal end 122. The leading portion 118 is joined to an intermediate portion of the shaft 120 which is free from threads and is joined to a trailing portion 124 of the shaft 116. The trailing portion 124 has threads 121 and joins the leading portion 118 of the shaft to a compression head 130 which also includes threads 123 at the same pitch and shape as the threads 121 of the trailing portion. The head 130 also forms a cone 133 that is threaded and which joins the threaded cylindrical portion of the trailing section of the shaft 116. The head 130 has a driving surface 132 in a drive recess 134 formed in the top of first end 112.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A surgical method for facilitating fusion between an intermediate phalange and a distal phalange comprising:
   implanting a compression screw comprising a spiked tip along a longitudinal axis of the distal phalange;
   placing the distal phalange at a selected angle relative to a longitudinal axis of the intermediate phalange such that the distal phalange is bent relative to the intermediate phalange, and
   driving the spiked tip of the compression screw into the intermediate phalange at the selected angle,
   wherein the compression screw comprises a threaded first portion, an unthreaded second portion, and a threaded third portion along a longitudinal axis of the screw, the threaded first portion including a conical head and a shaft having a constant minor diameter, the unthreaded second portion including a shaft having a constant outer diameter that is the same as the minor diameter of the shaft of the threaded first portion, and the threaded third portion including the spiked tip that terminates at a conical tip.

2. The surgical method as set forth in claim 1 wherein an angle of the conical head is greater than an angle of the conical tip.

3. The surgical method as set forth in claim 1 wherein a thread of the first portion extends along the conical head and the shaft.

4. The surgical method as set forth in claim 3 wherein the shaft of the first portion has a constant major diameter.

5. The surgical method as set forth in claim 3 wherein a thread of the third portion is continuous.

6. The surgical method as set forth in claim 3 wherein the thread along the conical head defines a conical head maximum major diameter, and the thread along the shaft of the threaded first portion defines a first portion major diameter, the conical head maximum major diameter being greater than the first portion major diameter.

7. The surgical method as set forth in claim 3 wherein the thread of the first portion is continuous.

8. The surgical method as set forth in claim 1 wherein at least the shaft of the the first portion or the shaft of the second portion is non-cannulated.

9. The surgical method as set forth in claim 1 wherein the method is performed percutaneously.

10. The surgical method as set forth in claim 1 wherein the thread of the first portion is a buttress thread.

11. The surgical method as set forth in claim 1 wherein the conical head comprises a taper with an angle from 5° to 12°.

12. The surgical method as set forth in claim 11 wherein an angle of the conical head is greater than an angle of the conical tip.

13. The surgical method as set forth in claim 1 wherein the conical head has a first length along the longitudinal axis of the screw and the threaded third portion has a second length along the longitudinal axis of the screw, the first length being smaller than the second length.

14. The surgical method as set forth in claim 1 wherein at least the second and third portions are non-cannulated.

* * * * *